United States Patent [19]

Bey et al.

[11] Patent Number: 4,935,449

[45] Date of Patent: Jun. 19, 1990

[54] N-2,3-BUTADIENYL TRI- AND TETRAAMINOALKANE DERIVATIVES

[75] Inventors: Philippe Bey; David M. Stemerick; Michael L. Edwards, all of Cincinnati; Alan J. Bitonti, Maineville, all of Ohio

[73] Assignee: Merrell Dow Pharmaceuticals Inc., Cincinnati, Ohio

[21] Appl. No.: 228,620

[22] Filed: Aug. 4, 1988

[51] Int. Cl.$^5$ .................. A61K 31/13; C07C 87/24
[52] U.S. Cl. ............................ 514/671; 514/673; 514/674; 514/895; 564/509
[58] Field of Search ............... 564/509; 514/895, 674, 514/671

[56] References Cited

U.S. PATENT DOCUMENTS 4,551,550  11/1985  Bey .......................... 564/509 X

Primary Examiner—Robert V. Hines
Attorney, Agent, or Firm—Stephen L. Nesbitt

[57] ABSTRACT

The importance of polyamines in biological systems is discussed as well as the implications of polyamines in the treatment of various diseases. Novel N-substituted-2,3-butadienyl tri- and tetra-aminoalkanes are disclosed as well as their use inthe treatment of diseases and the pharmaceutical compositions.

9 Claims, No Drawings

N-2,3-BUTADIENYL TRI- AND TETRAAMINOALKANE DERIVATIVES

FIELD OF INVENTION

This invention relates to novel chemical compounds which are derivatives of N-2,3-butadienyl tri- and tetraaminoalkanes. The compounds have useful pharmacologic properties.

BACKGROUND OF THE INVENTION

Although the polyamines, spermine and spermidine, were originally identified as constituents of seminal fluid and named accordingly, it is well known that these polyamines and their precursor, putrescine, are ubiquitous components of mammalian cells. The enzymatic reactions leading to the formation and interconversion of the polyamines have now been characterized. See, for example, P. McCann et al, eds "Inhibition of Polyamine Metabolism", Academic Press, Inc., Harcourt Brace Jovanovich, New York 1987. These reactions in mammalian cells and protozoa are generally similar to those found in plants and in bacteria, although there are some important differences, such as the absence from mammals of arginine decarboxylase as a route to putrescine via agmatine. Early studies, showing an increased accumulation of putrescine and spermidine in cells during growth and a large and rapid increase in the activity of ornithine decarboxylase (ODC) after application of growth promoting stimuli, suggested that polyamines may play a critical role in cell proliferation. This correlation has now been confirmed more directly in several ways. CHO cell mutants have been obtained which lack functional ODC and these were found to be non-viable in the absence of putrescine or spermidine. Compounds which prevent the synthesis of polyamines have been synthesized and shown to have a profound inhibitory action on cell proliferation. Such inhibitors of polyamine biosynthesis have been searched for and studied intensively over the past 20 years but the major breakthrough in the polyamine field is directly attributable to the synthesis of enzyme-activated irreversible inhibitors of ODC. The availability of these inhibitors has permitted many experiments providing new insight into the function of polyamines and their importance in cellular physiology.

The interconversion and degradation of polyamines is brought about by the action of an intracellular FAD-dependent polyamine oxidase. Its substrates are the $N^1$-acetylated derivatives of spermidine and spermine. Therefore, the extent to which these reactions occur is regulated by the activity of PAT which is very highly inducible by an excess of polyamines and by a variety of substances causing cell damage. These reactions allow for the rapid reduction of cellular polyamine concentrations but also permit the reutilization of the putrescine component of the polyamines. This recycling may be of physiological importance since there was a significant decline in tissue spermidine content when $N^1,N^4$-bis-(2,3-butadienyl)-1,4-butanediamine, a potent inhibitor of polyamine oxidase, was combined with α-difluoromethylornithine which inhibits ODC.

Another method of blocking polyamine synthesis has been developed by Porter and colleagues who found that certain synthetic derivatives of polyamines such as $N^1,N^8$-bis(ethyl)spermidine and $N^1,N^{12}$-bis(ethyl)spermine mimic the action of their parent polyamines in the repression of ODC and AdoMetDC. Exposure of cells to these compounds therefore leads to the depletion of the natural polyamines. However, these bis(ethyl) analogs will not support growth of L1210 cells and may have some potential as anti-tumor agents and for investigation of the functions of the polyamines which are critical for cell proliferation.

One of the more rewarding areas of recent research in polyamines has been elucidating their role in protozoal growth. The first indication of the impact that parasitic protozoa would have on the polyamine field was the discovery that DMFO would totally cure acute infections of the African trypanosome *T. b. brucei* in mice. This dramatic finding led to the remarkably swift use of DFMO in what would have been fatal cases of drug resistant late-stage human sleeping sickness in Africa.

A number of the Sporozoea class of protozoa have been shown to be sensitive to the effects of DFMO including Eimeria spp. and the distantly related *Pneumocystis carinii*. However, some of the most interesting findings have been with the Plasmodia spp., agents of malaria, the most widely distributed and prevalent parasitic disease in the world today. Although original findings from several laboratories have indicated no curative effects of DFMO on erythroacytic forms of malaria in vivo (*P. gallinaceum* in chickens, and *P. berghei* in mice), DFMO will block erythrocytic replication (schizogony) in culture in vitro and has recently been shown to significantly reduce parasitemia in *P. berghei* infections. Interestingly, when exoerythrocytic schizogony (i.e., in liver cells) was studied, DFMO would not only inhibit the cycle in the liver of infected mice, but would also completely inhibit the sporogonous cycle in the mosquito vector. Thus, malaria may well prove to be a significant target for use of inhibitors of polyamine biosynthesis and function.

Applicants have now discovered a novel class of PAO inhibitors.

SUMMARY OF THE INVENTION

This invention relates to novel N-substituted 2,3-butadienyl tri- and tetra-aminoalkanes of the formula

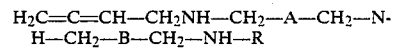

wherein A and B are each independently a bond or a $(C_1-C_8)$alkylene or $(C_2-C_8)$alkenylene group and
R is a methyl, ethyl, propyl, 2-propenyl, or 2,3-butadienyl group or
R is a group of the formula

wherein D is a bond or a $(C_1-C_8)$alkylene or $(C_2-C_8)$alkenylene group and
R' is a hydrogen, methyl, ethyl, propyl, acetyl, 2-propenyl, or 2,3-butadienyl group or a pharmaceutically acceptable salt thereof. This invention in other aspects relates to the ability of these compounds to act as inhibitors of polyamine oxidase. In yet another aspect, this invention relates to pharmaceutical compositions containing the novel compounds and to their preparation.

DETAILED DESCRIPTION OF THE INVENTION

As used herein the term "$(C_1-C_8)$alkylene" means straight and branched alkylene groups of from 1 to 8 carbon atoms wherein the open valencies can be on the same or different carbon atoms. Examples include methylene, 1,2-ethanediyl(ethylene), 1-methyl-1,2-ethanediyl(propylene), 1,2-propanediyl, 1,1-ethanediyl-(ethylidine), 1-methylpropylidene(secbutylidene), 1,1-propanediyl(propylidene), 2,2-dimethylpropylidene(-neopentylidene), 2-methyltrimethylene, 1,8-octanediyl, and 1,6-hexanediyl.

As used herein the term "$(C_2-C_8)$alkenylene" means straight and branched alkenylene groups of from 2 to 8 carbon atoms wherein the open valencies can be on the same or different carbon atoms. Examples include ethenylene(1,2-ethenediyl), 1,3-propenediyl(propenylene), and 1,3-butadiene-1,3-diyl.

As with any class of pharmaceutical compounds, some of the compounds or some of the subclasses of compounds are preferred over others. Of those compounds of formula 1, applicants prefer those wherein A and B, as well as D if present, are straight chain alkylene groups. Of these applicants prefer those compounds of formula 1 wherein A and B are each a one or two carbon atom straight chain alkylene group. Also preferred are those compounds of formula 1 wherein R is a —CH$_2$—D—CH$_2$—NHR' and wherein A and D are each a one or two carbon atom straight chain alkylene group, and of these, applicants especially prefer those compounds wherein B is a five to eight carbon atom straight chain alkylene group. Moreover applicants prefer those compounds of formula 1 wherein R is a methyl, ethyl or propyl group or wherein R is a 2,3-butadienyl group as well as those compounds wherein R is a —CH$_2$—D—CH$_2$—NHR' and wherein R' is a methyl, ethyl or propyl group or wherein R' is a 2,3-butadienyl group.

Examples of compounds included within the scope of this invention are:
3,3-1,5-9-triaza-1,9-bis-(2,3-butadien-1-yl)nonane,
4,4-1,6,11-triaza-1,11-bis-(2,3-butadien-1-yl)undecane,
3,8,3-1,5,14,18-tetraaza-1,18-bis-(2,3-butadien-1-yl)octadecane,
2,8,2-1,3,13,16-tetraaza-1,16-bis-(2,3-butadien-1-yl)hexadecane,
3,6,3-1,3,11,16-tetraaza-1,16-bis-92,3-butadien-1-yl)hexadecane.

Illustrative examples of pharmaceutically acceptable salts of the compounds of this invention include non-toxic acid addition salts formed with inorganic acids, such as hydrochloric, hydrobromic, sulfuric and phosphoric acid, or with organic acids, such as organic carboxylic acids, for example, salicylic, maleic, malonic, tartaric, citric and ascorbic acids and organic sulfonic acids, for example, methane sulfonic acid.

In general, the compounds of formula 1 can be prepared by deprotecting a compound of formula 2:

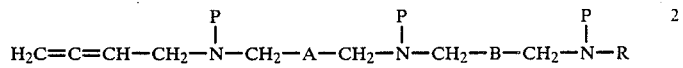

wherein A, B and R are as defined for formula 1 and wherein P is an amino-protecting group in a known manner to be useful for removing the amino-protecting groups, P.

The amino-protecting groups P are chosen with regard to the nature of the relevant reactions used to prepare the particular compounds of formula 2 and having regard to the ease of their removal. The protecting groups include lower alkanoyl, e.g., acetyl, propionyl and trifluoroacetyl; aroyl, e.g., benzoyl, toluoyl; lower alkoxycarbonyl, for example, methoxycarbonyl, ethoxycarbonyl and tertiobutoxycarbonyl; carbobenzoxy; benzenesulfonyl; and tosyl.

In the preparation of the compounds of formula 2, the protecting groups are introduced in a known manner such as the reaction of an appropriate primary or secondary amine with a lower alkanoyl or aroyl chloride anhydride, sulfonyl chloride, tertiobutoxycarbonyloxyimino-2-phenylacetonitrile (BOC—ON), or di-tertiobutyldicarbonate[(BOC)$_2$O]. A preferred amino-protecting group is tertiobutoxycarbonyl (BOC).

Removal of the protecting groups from the compounds of formula 2 is conducted in a manner known to those skilled in the art for the relevant protecting group. Usually, said removal involves hydrolytic cleavage using an organic or mineral acid such as trifluoroacetic acid, hydrochloric acid and the like; or by hydrogen chloride gas under anhydrous conditions. Solvents used will be chosen dependent upon the conditions of protecting group removal. For example, ethers such as diethylether can be used for cleavage with hydrogen chloride gas. If other acid sensitive functional groups are present in the molecule, the acid conditions chosen for the removal of the protecting group must be mild in order to avoid unwanted side reactions. In the case of a carbobenzoxy protecting group, this group can be removed in a known manner via catalytic hydrogenolysis.

The compounds of formula 2 wherein R is hydrogen or is —CH$_2$—D—CH$_2$NHR' and R' is hydrogen and P is tertiobutyloxycarbonyl (BOC) are prepared by the method depicted below in Scheme 1 starting with a N-tertiobutyloxycarbonylomegaaminocarboxylic acid as depicted in formula 3:

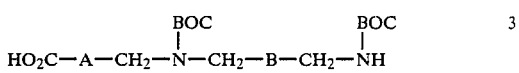

wherein A and B are as defined in formula 1.

SCHEME 1

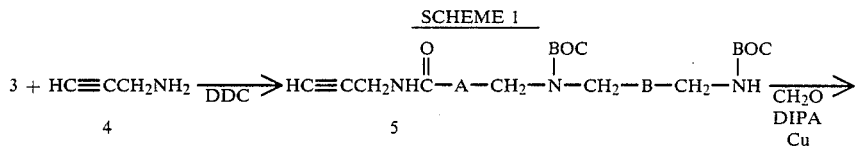

SCHEME 1

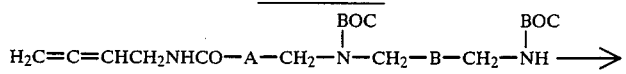
6

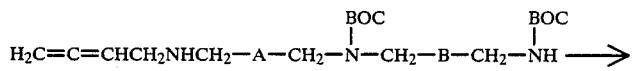
7

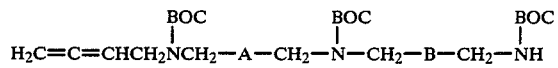
8

In the first step of Scheme 1, a compound of formula 3 is reacted in a known manner with propargylamine (4) to yield a compound of formula 5. The reaction is conveniently performed in the presence of N,N¹-dicyclohexylcarbodiimide (DCC) in an organic solvent, for example, acetonitrile. The ethynyl group of compound 5 can be converted to the allenyl group of compound 6 in a known manner using the general method described by P. Crabbe et al., *J.C.S. Chem. Comm.* 859–860 (1979) and H. Fillion et al., *Tet. Letters*, 929–930 (1980) for allenic alcohols. In accordance with this procedure the amino protected derivative of a compound of formula 5 is treated with formaldehyde and a secondary amine having a hydrogen atom on the α-carbon atom and heated in an organic solvent in the presence of an inorganic salt. Preferably, the heating utilizes reflux conditions. The preferred amine is diisopropylamine (DIPA) and the preferred inorganic salt is a copper salt, particularly cuprous bromide or cupric chloride. Suitable solvents include dioxane, tetrahydrofuran, 1,2-dimethoxyethane, benzene, acetonitrile and/or toluene. The conversion is deemed to proceed via the corresponding amino protected derivative of the secondary amino propynyl compound.

Compound 6 is selectively reduced in the third step in a known manner to a compound of formula 7. The reduction of the carbonyl group is conveniently achieved by means of lithium aluminum hydride in diethyl ether. Compound 7 can thus be converted in a known manner to a compound of formula 8 utilizing conventional procedures for the introduction of a BOC protecting group on a secondary amine. Thus, for example, the secondary amine can be protected by treatment with ditertiobutyl-carbonate in tetrahydrofuran (THF) or dichloromethane.

In general, the compounds of formula 2 wherein R is —CH₃, —CH₂CH₃, or —CH₂CH₂CH₃, —CH₂CH=C=CH₂, or —CH₂CH=CH₂ are prepared in a known manner by the reaction of an N-protected-2,3-butadienylamine of formula 9:

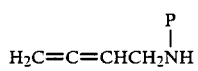
9 wherein P is an amino-protecting group, with a compound of formula 10:

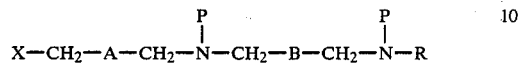
10 wherein A and R are as defined in formula 1, P is an amino-protecting group, and X is a leaving group.

Preferred leaving groups are mesylate, tosylate, bromide, or iodide. Iodide is the most preferred leaving group. The reaction can conveniently be carried out in an organic solvent, such as tetrahydrofuran (THF), diethyl ether, dimethylformamide (DMF), or benzene, in the presence of one equivalent of strong base, such as, potassium or sodium hydride, potassium or sodium tert-butoxide, or lithium diisopropylamide, for a period ranging from 10 minutes to 24 hours at −30° C. to 100° C. optimally in the presence of a catalytic amount of sodium iodide. The preferred reaction conditions utilize sodium hydride in DMF at 0° C. to 25° C.

The compounds of formula 2 wherein R is —CH₂CH=C=CH₂, can also be prepared by the reaction of two equivalents of a compound of formula 9 with a compound of formula 11:

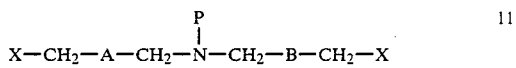
11 wherein A and B are as defined in formula 1, X is a leaving group, such as those defined with respect to formula 10, and P is an amino-protecting group, preferably BOC. This reaction can be conducted in a known manner as previously described with respect to the reaction of a compound of Formula 9 with a compound of formula 10.

The compounds of formula 2 wherein R is —CH₂—D—CH₂NHR' and R' is acetyl or hydrogen are made in a manner known per se by the reaction sequence depicted below in Scheme 2 starting from a compound of formula 8 (see Scheme 1):

SCHEME 2

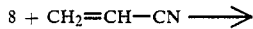
1

SCHEME 2

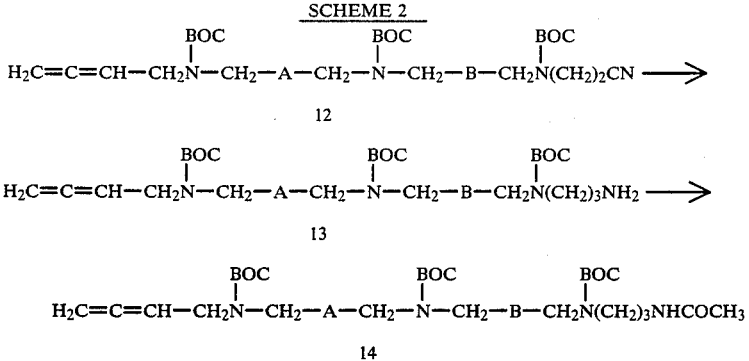

In the first step of Scheme 2, a compound of formula 8 is reacted with acrylonitrile (11) in a known manner to provide the compound of formula 12. The reaction is performed in the presence of a base in an organic solvent.

In the second step of Scheme 2, compound 12 is reduced to yield the compound of formula 13 in a known manner utilizing conventional (non-catalytic) methods for the selective reduction of a cyano group to a primary amino group. The preferred reagent is lithium aluminum hydride. The preparation of the N-acetyl derivative of formula 14 from compound 13 is carried out in a manner known to those skilled in the art using conventional acetylation techniques.

The N-protected 2,3-butadienyl amine compounds of formula 9 can be prepared in a known manner from an N-protected propargyl amine of formula 15:

wherein P is an amino-protecting group as previously defined. The procedure for carrying out this transformation is described above with respect to the second step of Scheme 1.

The compounds of formula 1 are irreversible inhibitors of polyamine oxidase (PAO) as can be demonstrated in vitro and in vivo in biochemical test procedures. The biochemical testing of illustrative compounds for their ability to inhibit PAO is illustrated herein in Example 3.

Inhibitors of PAO are of particular interest for the study of the physiological role of the polyamine interconversion pathways in mammals. Additionally, inhibitors of PAO prevent the degradation of $N^1$-acetylspermidine with the concomitant formation of putrescine. The ability to decrease the amount of circulating putrescine in mammals would be highly advantageous with certain conditions, such as, for example, in situations of enhanced cell proliferation.

It is believed that the compounds of formula 1 are "substrate-induced irreversible inhibitors" of PAO. Such inhibitors are also known in the art as "enzyme-activated irreversible inhibitors", "suicide enzyme inhibitors", "$K_{cat}$ inhibitors", or "mechanism-based inhibitors". In order for a compound to be substrate-induced irreversible enzyme inhibitor, the compound must be a substrate for the target enzyme, and the compound must contain a latent reactive group susceptible to being unmasked as the result of the normal catalytic action of the enzyme. The unmasking of the latent reactive group by the action of the enzyme generates a reactive function which alkylates a nucleophilic residue present at the active site of the enzyme. Thus, there is formed a covalent bond between the inhibitor and the enzyme at the active site resulting in irreversible inactivation of the enzyme. Such inhibitors are extremely specific since the inhibitor must be a substrate for the target enzyme and since biotransformation of the inhibitor by the target enzyme is required before the enzyme is inactivated.

Although it is believed that the compounds of formula 1 generally exert their action by means of a substrate-induced mechanism, inhibition may occur by other mechanisms, such as by competitive inhibition.

By virtue of the potent PAO inhibition activity, the compounds of this invention interrupt polyamine synthesis in both plant and animal systems. The compounds are useful in the treatment of Plasmodium Falciporium infections and in the treatment of other diseases and conditions. The compounds inhibit PAO when employed in a concentration of from about 1 to about 100 micromolar.

The amount of the active ingredient to be administered can vary widely according to the particular dosage unit employed, the period of treatment, the age and sex of the patient treated and the nature and extent of the disorder treated. The total amount of the active ingredient to be administered will generally range from about 5 mg to about 500 mg per day. A unit dosage may contain from 25 to 500 mg of active ingredient, and can be taken one or more times per day. The active compound of formula 1 can be administered with a pharmaceutical carrier using conventional dosage unit forms either orally, parenterally, or topically.

For oral administration the compounds can be formulated into solid or liquid preparations such as capsules, pills, tables, solutions, tablets, troches, lozenges, melts powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the breakup and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intented to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptable surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically acceptable adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 7. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

EXAMPLES

The following nonlimiting examples illustrate various aspects of this invention.

EXAMPLE 1

N-2,3-BUTADIENYL-N'-[3-(2,3-BUTADIENYLAMINO)PROPYL]-1,3-PROPANEDIAMINE TRIHYDROCHLORIDE

Bis-(3-hydroxypropyl)amine was converted to the BOC derivative with di-t-butyldicarbonate. The BOC derivative (11.5 g, 0.05 mol) and triethylamine (18.5 g, 0.18 mol) were dissolved in dichloromethane (500 ml) and the solution was chilled to 0° C. A solution of methanesulfonyl chloride (12.5 g, 0.11 mol) in dichloromethane (85 ml) was added dropwise. Mixture was stirred 1.5 hours, diluted with dichloromethane (250 ml) and extracted with 1N acetic acid, aq. NaHCO$_3$, H$_2$O and brine. Organic layer was dried and evaporated and the residue was purified on a flash silica gel column, eluted with EtOAc/hexane (3/2) to give 8.8 g of white solid N-butyloxycarbonyl-bis-(3-mesyloxypropyl)amine. Anal. (C$_{13}$H$_{27}$NO$_8$S$_2$) C, H, N, S.

Sodium iodide (6.7 g, 44 mol), NaH (1.96 g of 60% dispersion in oil, 49 mmol) and compound N-butyloxycarbonyl- bis-(3-mesyloxypropyl)amine (8.8 g, 22 mmol) were added to DMF (50 ml) and mixture was chilled to 0° C. A solution of the allenyl compound N-butyloxycarbonyl-N-(2,3-butadienyl)amine (8.3 g, 48 mmol) in DMF (20 ml) was added and the mixture was stirred at 0° C for 3.5 hours. The solvent was removed, the residue was taken up in EtOAc and the solution was extracted with H$_2$O. The organic layer was dried and evaporated. Flash chromatography (25% EtOAc/hexane) of the residue gave 7.9 g of a thick oil, the bis BOC derivative of the title compound.

The bis BOC derivative was dissolved in EtOH (35 ml), a solution of HCl in ether (120 ml, 2N) was added and the mixture was stirred 18 hours at ambient temperature. The mixture was filtered and the precipitate was vacuum dried at reduced pressure over P$_2$O$_5$ to give the product as the trihydrochloride, mp 273°–275° C. (dec.) Anal. (C$_{14}$H$_{25}$N$_3$.3HCl) C, H, N, Cl.

In a like manner, but starting with bis(2-hydroxyethyl)amine and following the same sequence of reactions, one obtains the compound N-2,3-butadienyl-N'-[2(2,3-butadienylamino)ethyl]-1,2-ethanediamine trihydrochloride.

In a like manner, but starting with bis(4-hydroxybutyl)amine, one obtains the compound N-2,3-butadienyl-N'-[4-(2,3-butadienyl(amino)butyl]1,4-butanediamine.

EXAMPLE 2

1,18-BIS(2,3 BUTADIENYL-1-YL)-5,14,18-TETRAAZAOCTADECANE TETRAHYDROCHLORIDE

The diol N,N'-bis-t-butoxycarbonyl-N,N'-bis(3-hydroxypropyl)-1,8-diaminooctane, was converted to a dimesylate and the dimesylate was reacted with two equivalents of N-t-butoxycarbonyl-2,3-butadienylamine. The product was deblocked by use of ethanolic HCl to give the tetrahydrochloride salt, mp 286°–287° C. (dec).

Anal: Calcd for C$_{22}$H$_{42}$N$_4$.4HCl: C, 51.96; H, 9.12, N, 11.02; Cl 27.89. Found: C, 51.80: H, 9.12: N, 11.12; Cl, 27.73.

By a similar sequence the following starting materials may be converted to the products named A. Starting:
N,N'-bis-t-butoxycarbonyl-N,N'-bis-(3-hydroxypropyl)-1,7-diamine heptane
Product: 1,17-bis(2,3-butadienyl-1-yl)-1,5,13,17-tetraazaheptadecane tetrahydrochloride B. Starting:
N,N'-bis-t-butoxycarbonyl-N,N'-bis(2-hydroxyethyl)-1,8-diaminooctane
Product: 1,16-bis(2,3-butadienyl-1-yl)-1,4,13,16-tetraazahexadecane

N,N'-BIS-t-BUTOXYCARBONYL-N,N'-BIS-(3 HYDROXYPROPYL)-1,7-DIAMINOHEPTANE

N,N'-Bis-(3-hydroxypropyl),N,N'-dibenzyl-1,7-diaminoheptane (26.9 g, 0.063 mole) was dissolved in ethanol (220 ml) and hydrogenated on a Parr hydrogenation apparatus in presence of Pd(OH)$_2$ (Pearlman's catalyst) (0.5 g). After theoretical uptake of hydrogen had occurred, the mixture was filtered and the filtrate was evaporated. The residue was redissolved in dichloromethane (300 ml) and di-t-butyldicarbonate (44 g, 0.2 mole) was added and the mixture was stirred for 18 hours. The solvent was removed on a rotary evaporator and the residue was purified by flash chromatography (silica gel, EtOAc/toluene, 4/1) to give the product (22 g) as a gum. A mass spectrum shows molecular ion (M+1) at 447.

Anal: Calcd for $C_{23}H_{46}N_2O_6$: C, 61.85; H, 10.38; N, 6.27. Found: C, 62.04; H, 10.26; N, 6.25.

By the same procedure using N,N'-bis(3-hydroxypropyl)N,N'-dibenzyl-1,8-diaminooctane one obtains N,N'-bis-t-butoxycarbonyl-N,N'-bis(3-hydroxypropyl)-1,8-diamine.

By the same procedure using N,N'-bis(4-hydroxybutyl)-N,N-dibenzyl-1,7-diamino heptane one obtains N,N'-bis-t-butoxycarbonyl-N,N'-bis(4-hydroxybutyl)-1,7-diamino heptane.

N,N'-BIS-(3-HYDROXYPROPYL)-N,N'-DIBENZYL-1,7-DIAMINOHEPTANE

A mixture of N,N'-dibenzyl-1,7-diamine heptane (26 g, 0.084 mole), 1-chloro-3-hydroxypropane (15.9 g, 0.168 mole), sodium carbonate (53 g, 0.50 mole), sodium iodide (1.2 g) and n-butanol (40 ml) was heated at reflux for 20 hours. The mixture was cooled and diluted with a mixture of dichloromethane (700 ml) and water (500 ml). The organic layer was separated, dried and evaporated. The residue was purified by flash chromatography (silica gel, EtOAc/MeOH (10/1)) to give the product (26.9 g) as a thick gum. Mass spectrum shows molecular ion (M+1) 427.

Anal: Calcd for $C_{27}H_{42}N_2O_2$: C, 76.01; H, 9.92; N, 6.57. Found: C, 76.26; H, 9.91; N, 6.77.

Using the same conditions with N,N'-dibenzyl-1,8-diaminooctane one obtains N,N'-bis(3-hydroxypropyl)-N,N'-dibenzyl-1,8-diaminooctane.

Using the same conditions with 1-chloro-2-hydroxyethan or -chloro-4-hydroxybutane in place of 1-chloro-3-hydroxypropane one obtains N,N'-bis(2-hydroxyethyl)-N,N'-dibenzyl-1,7-diaminoheptane and N,N'-bis(4-hydroxybutyl)-N,N'-dibenzyl-1,7-diaminoheptane.

N,N'-DIBENZYL-1,7-DIAMINOHEPTANE

A solution of benzaldehyde (46 g, 0.44 mole) and 1,7-diamine heptane (26 g, 0.2 mole) in ethanol (200 ml) was hydrogenated on a Parr shaker hydrogenation apparatus in the presence of platinum oxide (0.5 g) until uptake of $H_z$ was equal to theoretical value for the reaction. The mixture was filtered, the filtrate was evaporated and the residue was distilled to obtain 27 g of product, $bp_{0.4}$ 185°.

In a similar manner starting with 1,8-diamine octane one obtains N,N'-dibenzyl-1,8-diamine octane.

EXAMPLE 3

The ability of the compounds of formula 1 to inhibit PAO ex vivo can be demonstrated according to the following test procedure:

MEASUREMENT OF PAO ACTIVITIES IN MOUSE TISSUES

PAO activity was measured ex vivo in mouse and rat liver homogenates using acetylspermine as substrate, following the method of Bolkenius, et al. (1985) *Bio. Chim. Biophys. Acta* 38: 69–76.

TABLE V

| | | Polyamine Oxidase Inhibition[1] | | | |
|---|---|---|---|---|---|
| | | | | | In Vivo |
| | | In Vitro Rat Liver Pao | | Dose | PAO Activity p/mol/min/mg |
| Compound | Structure | Ki, µM | τ$_{50}$, min | mg/kg | protein |
| 46 | ⇌⇌∖NH(CH$_2$)$_3$NH(CH$_2$)$_3$NH∕⇌⇌ | 3.0 | 4.0 | 1.0 | 1.0 |
| 51 | ⇌⇌∖NH(CH$_2$)$_3$NH<br>\|<br>(CH$_2$)$_8$<br>\|<br>⇌⇌∖NH(CH$_2$)$_3$NH | 2.5 | 2.0 | 1.0 | 4.1 |
| 56 | ⇌⇌∖NH(CH$_2$)$_4$NH∕⇌⇌ | 1.7 | 1.0 | 2.5 | 3.9 |
| | | | | 25.0 | 1.9 |

TABLE V-continued

| | | Polyamine Oxidase Inhibition[1] | | | |
| --- | --- | --- | --- | --- | --- |
| | | In Vitro Rat Liver Pao | | | In Vivo |
| Compound | Structure | $K_i$, $\mu M$ | $\tau_{50}$, min | Dose mg/kg | PAO Activity p/mol/min/mg protein |
| | Control | | | 0 | 18.7 |

Mice were dosed i.p. with drugs 24 hours prior to determination of PAO activity in the liver.
Rat liver polyamine oxidase was purified by the procedure of Holtta, E. (1977) Biochemistry 16:91-100 through the DEAE-cellulose chromatography step. $K_i$ and $\tau_{50}$ were determined using the partially purified PAO, as described by Bey et al. (1985) J. Med. Chem. 28:1.
Mouse livers were homogenized and PAO activity determined as described in Bolkenius et al. (1985) Biochim. Biophys. Acta 838:69-76.
Protein concentrations were estimated by the method of Bradford, M. (1976) Anal. Biochem. 72:248-254, using bovine serum albumin as the standard.

We claim:

1. A compound of the formula

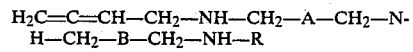

H—CH$_2$—B—CH$_2$—NH—R wherein A and B are each independently a bond or a $(C_1-C_8)$alkylene or $(C_2-C_8)$alkenylene group and R is a methyl, ethyl, propyl, 2-propenyl, or 2,3-butadienyl group
   or a pharmaceutically acceptable salt thereof.

2. A compound of claim 1 wherein R is a methyl, ethyl, propyl, or 2,3-butadienyl group and A and B are each independently a bond or a $(C_1-C_8)$alkylene group.

3. A compound of claim 1 wherein R is a methyl, ethyl, propyl, or 2,3-butadienyl group and A and B are each independently a bond or a $(C_1-C_2)$alkylene group.

4. A compound of claim 1 wherein R is a methyl, ethyl, propyl, or 2,3-butadienyl group and A and B are each a methylene group.

5. A compound of claim 1 wherein R is a 2,3-butadienyl group and A and B are each a methylene group.

6. A pharmaceutical composition comprising a compound of one of claims 1-5 and a pharmaceutically acceptable carrier.

7. A method of treating a malarial infection in a patient in need thereof which comprises administering to the patient an antimalarially effective amount of a compound of one of claims 1-5.

8. A method of inhibiting polyamine oxidase in a patient in need thereof which comprises administering to the patient a polyamine oxidase inhibitory effective amount of a compound of one of claims 1-5.

9. A method of inhibiting polyamine oxidase in a cell which comprises contacting the cell with an effective amount of a compound of one of claims 1-5.

* * * * *

UNITED STATES PATENT AND TRADEMARK OFFICE
CERTIFICATE OF

PATENT NO. : 4,935,449

DATED : June 19, 1990

INVENTOR(S) : Philippe Bey et al.

It is certified that error appears in the above-identified patent and that said Letters Patent is hereby corrected as shown below:

On the cover page, at line 5 in the Abstract, the patent reads "inthe" and should read --in the--. At column 2, line 58, the patent reads "($C_1$-$C_8$)alkylene Or" and should read --($C_1$-$C_8$)alkylene or--. At column 4, line 65, in Scheme 1 the patent reads $\underline{3}$ + HC≡CCH$_2$NH$_2$ $\xrightarrow{DDC}$ HC   and should read $\underline{3}$ + HC≡CCH$_2$NH$_2$ $\xrightarrow{DCC}$ HC At column 6, at line 60, Scheme 2 reads  8 + CH$_2$=CH-CN ⟶
and should read 8 + CH$_2$=CH-CN ⟶  1

11

At column 8, line 51, the patent reads "pills, tables, solutions, tablets, troches" and should read --pills, tablets, troches,--. At column 12, line 16, the patent reads "-chloro-4-hydroxybutane" and should read --1-chloro-4-hydroxybutane--.

Signed and Sealed this

Twenty-fourth Day of September, 1991

Attest:

HARRY F. MANBECK, JR.

Attesting Officer

Commissioner of Patents and Trademarks